US009759735B2

(12) United States Patent
Csikos et al.

(10) Patent No.: US 9,759,735 B2
(45) Date of Patent: Sep. 12, 2017

(54) DEVICE FOR THE HANDLING OF SAMPLES CONTAINING LIQUID COMPONENTS

(71) Applicant: NORMA DIAGNOSZTIKA KORLÁTOLT FELELÖSSÉGÜ TÁRSASÁG, Budapest (HU)

(72) Inventors: Jeno Csikos, Budapest (HU); Peter Kovacs, Budapest (HU); Balint Tibor Mendele, Budapest (HU); Laszlo Orban, Budapest (HU); Laszlo Sule, Budapest (HU); Peter Toth-Miklos, Budapest (HU); Attila Zsolt Tremmel, Siofok (HU); Gabor Varnagy, Budapest (HU)

(73) Assignee: NORMA INSTRUMENTS ZÁRTKÖRűEN MűKÖDő RÉSZVÉNYTÁRSÁSAG, Miskolc (HU)

( * ) Notice: Subject to any disclaimer, the term of this patent is extended or adjusted under 35 U.S.C. 154(b) by 0 days.

(21) Appl. No.: 14/442,347

(22) PCT Filed: Nov. 6, 2013

(86) PCT No.: PCT/HU2013/000106
§ 371 (c)(1),
(2) Date: May 12, 2015

(87) PCT Pub. No.: WO2014/072757
PCT Pub. Date: May 15, 2014

(65) Prior Publication Data
US 2016/0274138 A1     Sep. 22, 2016

(30) Foreign Application Priority Data

Nov. 12, 2012   (HU) .................................... 1200650

(51) Int. Cl.
*G01N 35/10* (2006.01)
*G01N 1/14* (2006.01)

(52) U.S. Cl.
CPC ........... *G01N 35/1079* (2013.01); *G01N 1/14* (2013.01); *G01N 35/1009* (2013.01); *G01N 2001/1418* (2013.01)

(58) Field of Classification Search
CPC .. G01N 35/1079; G01N 35/1009; G01N 1/14; G01N 2001/1418; G01N 33/49; A61J 1/2089; A61J 1/2096; A61J 1/201
See application file for complete search history.

(56) References Cited

U.S. PATENT DOCUMENTS

| 4,861,553 | A | * | 8/1989 | Mawhirt | .............. | G01N 35/021 198/802 |
| 5,555,920 | A | * | 9/1996 | Godolphin | ............ | A61J 1/2089 141/130 |

(Continued)

FOREIGN PATENT DOCUMENTS

WO   WO 95/06867   3/1995

*Primary Examiner* — Jill Warden
*Assistant Examiner* — Benjamin R Whatley
(74) *Attorney, Agent, or Firm* — Joseph G. Seeber

(57) ABSTRACT

A device for handling a sample containing liquid components comprises a housing, a retaining part-unit for holding a storage unit containing the sample, a drive unit for moving the retaining part-unit, and at least one sample-taking body located in the housing. The drive unit has a drive member and a movement-transfer part-unit connected tHereto, and the movement-transfer part-unit has at least one rotation axle. The drive member of the drive unit has a single drive motor, while the movement-transfer part-unit is adjacent to a carrying structure that rotates around the rotation axle(s) of the movement-transfer part-unit. A drive-transfer unit is inserted between the carrying structure and the drive motor, the carrying structure having first and second moving ele- (Continued)

Figure 1:
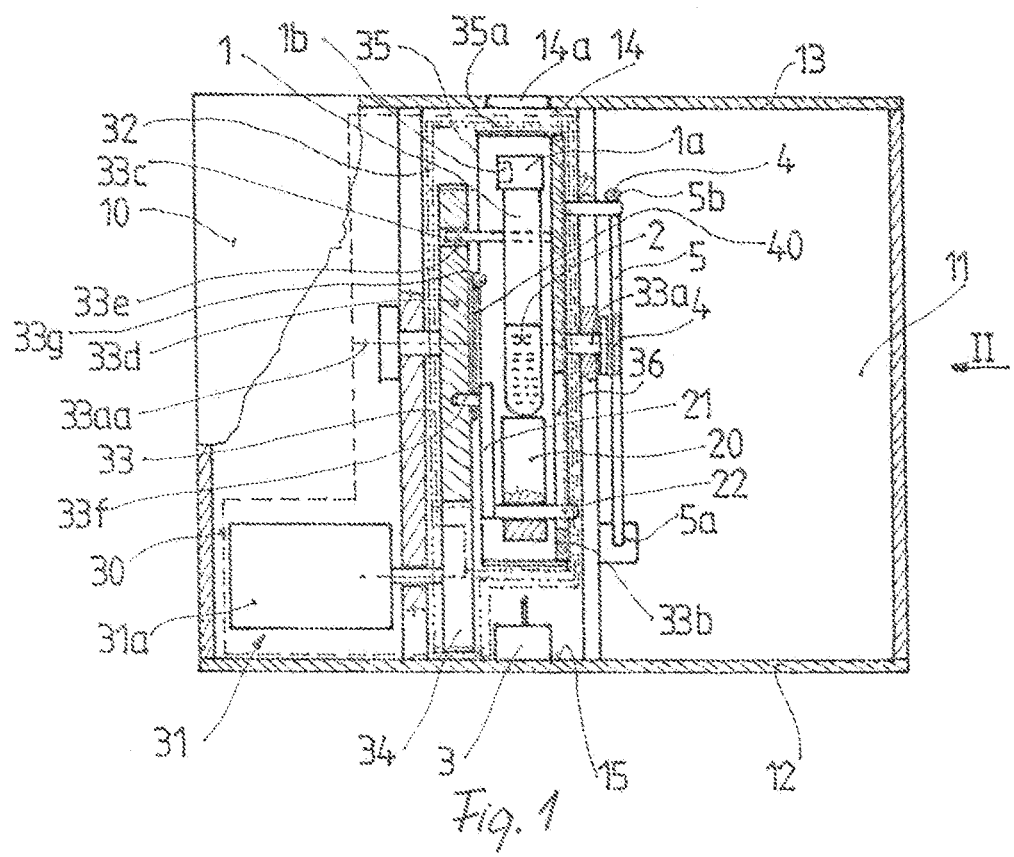

ments which have first and second control bodies, respectively, falling outside of first and second rotation axles, respectively. The first and second moving elements have a periodical, movement-transfer positive coupling link with each other.

20 Claims, 4 Drawing Sheets

(56) References Cited

U.S. PATENT DOCUMENTS

| | | | |
|---|---|---|---|
| 2005/0186119 A1* | 8/2005 | Itoh | G01N 35/1009 422/561 |
| 2011/0100501 A1* | 5/2011 | Mizuno | A61J 3/002 141/2 |
| 2013/0035658 A1* | 2/2013 | Haenggi | A61J 1/20 604/408 |

* cited by examiner

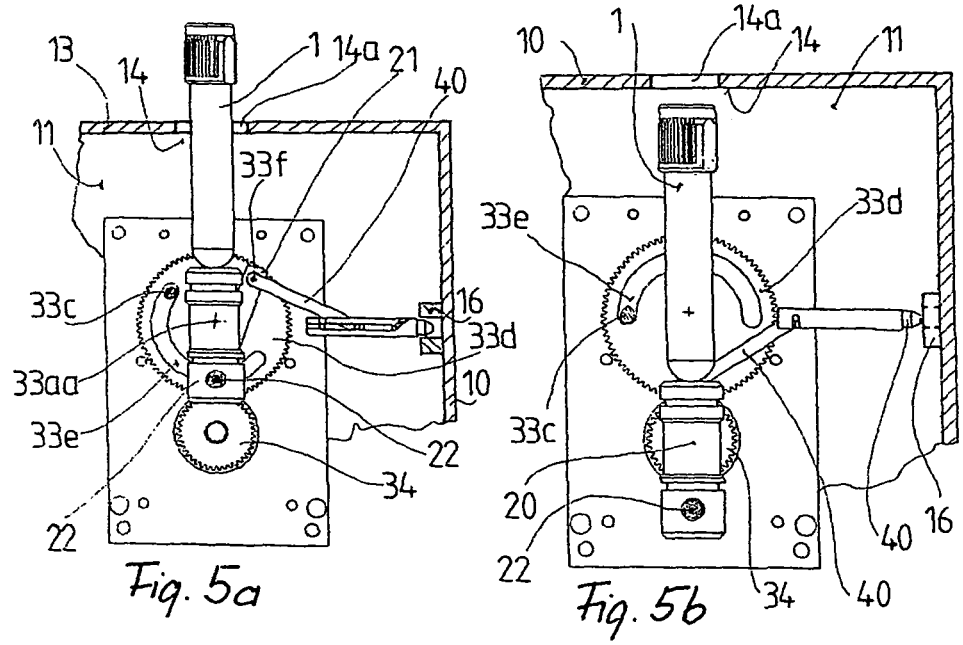
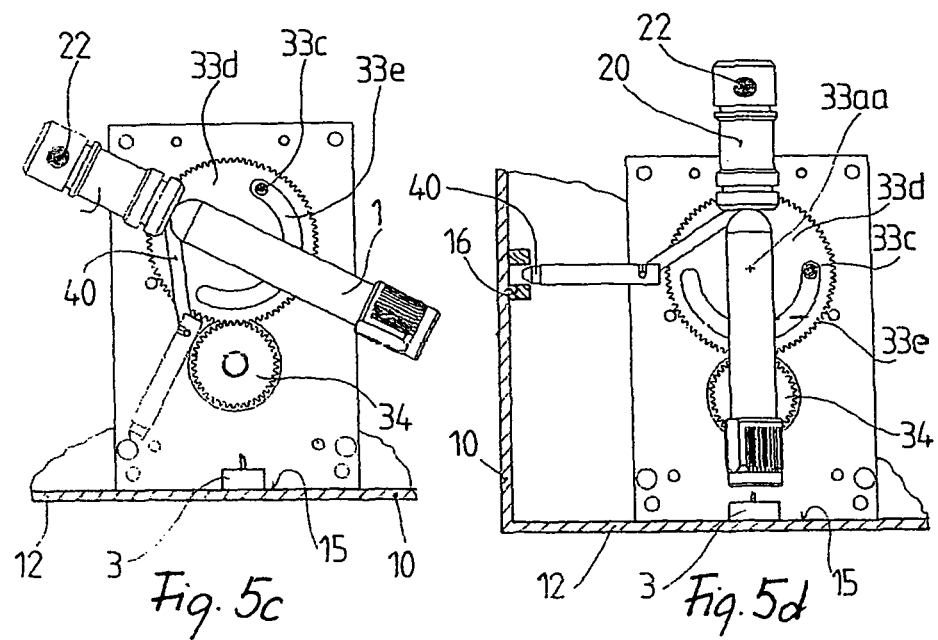

DEVICE FOR THE HANDLING OF SAMPLES CONTAINING LIQUID COMPONENTS

The subject of the invention relates to a device for handling samples containing liquid components, especially for performing sample-taking from blood, which contains a retaining part-unit serving to hold the storage unit containing the sample, a drive unit serving to move the retaining part-unit, as well as a housing encompassing at least a part of the drive unit, and at least one sample-taking body located in the internal space of the housing, where the drive unit has a drive member, and a movement-transfer part-unit in connection with the drive member, and the movement-transfer part-unit has at least one rotation axle.

Numerous devices have been developed to date for the testing of various compounds, compositions and of body fluids circulating in the circulation systems of the human body, so for the testing and analysis of blood and its components, among others. Such devices may be listed among those that make it possible to store, move and dispense the sample to be tested e.g. blood.

Publication document number JP 2011055916 presents a storage device with a cylinder-shaped shell formed in a harmonica-type way capable of flexible deformation encompassing an internal space which, due to the shell, is suitable for dispensing even small amounts of liquid material. The disadvantage of the solution is that due to its limited operation speed it is not suitable for serving high-output equipment and after dispensing a sample package it becomes essentially unusable.

Publication document number CN 102072930 includes a device suitable for the simultaneous testing of electrolytes in blood samples, in the case of which the tested sampled and the reagents used for the tests are transported to the testing point with the help of a multifunction dispensing valve. The part of this device serving transportation purposes is complex; it is constructed from complicated structural elements demanding precise working and the handling, maintenance of which requires suitable professional knowledge. And during operation there is a great possibility of breakdown due to the numerous moving structural parts.

Publication document number CN 102113886 relates to another multifunction blood sample testing device, which has a part-unit suitable for performing several tasks. Its disadvantage is that the movement of the storage pipe holding the sample can only be performed with difficulty, which limits the speed of dispensing and processing, as well as increasing the space demanded for the device.

Publication document number CN 102095841 presents a blood sample testing device in which the storage tube containing the sample is taken to the sealed sample-taking point containing the needle performing the sample-taking by a mechanism consisting of several moving units. However, the deficiency of the construction is that it contains a part-unit serving to realise numerous, different movements, as a consequence of which the device requires a lot of space, uses a significant amount of energy, and its risk of breakdown is high as its demand for maintenance as well.

Utility model specification number CN 201382946 presents a completely automated blood sample analysis device in the case of which the tube containing the sample is taken from the sample store to the testing station by a mechanism performing a lifting-turning-insertion movement. The disadvantage of this solution is also that several, independent moving part-units are required in order to take the storage unit holding the sample along the desired route between two points. Therefore, this version also demands a large amount of space, a large amount of energy and is prone to faults.

The patent specification number WO 95/06867 also presents an apparatus for aliquotting blood serum or blood plasma. This equipment uses at least two different drive motor for putting a pipetter to the stopper and moving the blood collection tube from the starting position to the end position. This solution also requires a special additional apparatus for pushing some gas to the internal part of the blood collection tube, which forces the collected blood to drop to the analyser cup. This solution has a difficult structure, demands a large amount of space, a large amount of energy and is prone to faults too.

Our aim with the construction according to the invention is to overcome the deficiencies of the known devices serving sample transportation and to create a version that solves the desired movement task of the storage units with a minimal drive unit in such a way that its space demand, energy demand is smaller than that of the usual devices, contains a minimal number of moving parts and, as a result of its simple construction, has a low probability of breakdown.

The recognition that led to the structure according to the invention was that if elements capable of rotating in a regulated way around suitably selected axles are linked to each other with the help of novel positive couplings so that the driven rotating structural element only moves the other structural elements associated with it in a certain range of rotation, then a drive motor performing a single rotational movement is sufficient so that the from-here-to-there movement of the storage unit containing the sample performed along a line and its rotation around an axis can be realised, with the help of which the storage unit can be precisely and quickly moved between the desired starting and terminal points, and so the task may be solved.

In accordance with the set aim the device according to the invention for handling samples containing liquid components, especially for performing sample-taking from blood,—which contains a retaining part-unit serving to hold the storage unit containing the sample, a drive unit serving to move the retaining part-unit, as well as a housing encompassing at least a part of the drive unit, and at least one sample-taking body located in the internal space of the housing, where the drive unit has a drive member, and a movement-transfer part-unit in connection with the drive member, and the movement-transfer part-unit has at least one rotation axle,—is set up in such a way so that the drive member of the drive unit has a single drive motor, while the movement-transfer part-unit is formed by the set of a carrying structure embedded so that it may rotate around the rotation axles of the movement-transfer part-unit, and a drive-transfer unit inserted between the carrying structure and the drive motor, furthermore, the carrying structure has a first moving element and a second moving element, where from among the first moving element and the second moving element, the first has a first control body falling outside of its own rotation axle, while the second has a second control body working together with the first control body and falling outside of its own rotation axle, and with the help of the second control body working together with the first control body, the first moving element and the second moving element have a periodical, movement-transfer positive coupling link with each other, furthermore, of the first moving element and the second moving element of the carrying structure, one of them is connected to a sliding fitting connected to the retaining part-unit serving to hold the storage unit, one of either the first moving element or the second moving element of the carrying structure has a first guide piece, while the retaining part-unit serving to hold the storage unit and/or the sliding fitting has a second guide piece, the first guide piece and the second guide piece are connected to one another, and the storage unit is periodically forced to a programmed movement path in this way, while either the first moving element or the second moving element is supplemented with a swivel pin falling outside of its rotation axle and containing the second control body, and the sliding fitting of the retaining part-unit and/or the locking structure is connected to the swivel pin in such a way so as to permit rotation, furthermore a locking structure is inserted between at least one of the first moving element and the second moving element of the carrying structure and the housing, and with the help of the locking structure one of the first moving element and the second moving element is temporarily firmly connected to the housing, and the sample-taking body is in the internal space of the housing located firmly with respect to the housing, and the sample-taking body is fixed in the lower part of the housing.

A further feature of the device according to the invention may be that sample-taking body is a short needle.

From the point of view of the invention it may be favourable if it is supplemented with a second sample-taking body, where at least a part of the second sample-taking body is inserted into a protective shell located in the internal space of the housing, and one section of the protective shell is fixed to the housing, while a second section of the protective shell is fixed to a carrying structure that is capable of moving as compared to the housing. The other sample-taking body is a flexible tube, e.g. Teflon tube.

In the case of a further embodiment of the device, a reading part-unit is located in the internal space of the housing in the vicinity of the movement path of the storage unit containing the sample, and a sensor part-unit is located in the vicinity of the filing zone of the storage unit containing the sample.

The device according to the invention has numerous advantageous characteristics. The most important of these is that as a consequence of the novel kinematic system, using the help of a single stepper motor it may be realised that the storage unit containing the sample is taken out of the sample holder, it is mixed, it is taken to the needle sample taking location, the desired amount of sample is taken out of the storage unit there under controlled, safe conditions, then the storage unit is removed from the device by moving it from the sample-taking position to an output position.

It is a significant advantage that as a result of the solution according to the invention sample-taking takes place from the storage unit while it is upside-down, i.e. from the direction of the sealing cap, therefore a short sampling needle is sufficient in order to take a precise sample, and during the operation no external physical effect is able to influence the physical or chemical condition of the sample taken.

An advantage related to this is that the penetrating needle is located in the closed, internal space of the device, therefore it cannot cause personal injury, as sample taking is realised automatically.

Another advantage due to the kinematic system used in the solution according to the invention is that during sample taking there is no needle movement; therefore there is no transient that would influence the sample. Due to upside-down sample-taking needle insertion, a special needle-point profile is not needed for removing any air from sample holder tube; therefore, the sample-taking needle may be of the same structure as a standard injection needle.

Another advantage that may be listed is that the device according to the invention—as a consequence of the unique structural element linked with novel connections—using the single drive motor is able to rotate the storage unit so that the stored sample is suitably mixed, which before sample-taking results in homogenising the sample, and this is an important circumstance form the point of view of the assessment and analysis of the sample.

It is also favourable that the sample tubes may be inserted in any desired position and may be issued even at the same place or elsewhere, so an automatic storage unit feed adapter may be easily fitted to the device.

Another advantage that must be highlighted is that the device according to the invention is suitable for both closed tube insertion and open tube sample taking, and the flexible tube only protrudes from the device if there is an express need for it.

Another feature that may be mentioned among the advantages is that due to the kinematic system it is possible to read the identifiers, e.g. barcodes, placed on the storage units during sample taking, which greatly increases speed and reliability of processing.

Also due to the application of the novel kinematic system according to the invention is that due to the single drive motor that device may fit in a small space, its energy consumption is significantly lower that the known versions and as a result of the small number of moving parts, its breakdown probability is also minimal.

A further advantage deriving front this is the favourable operation and maintenance costs.

Another feature that must be listed among the advantages is that the importance structural elements of the device may be simply manufactured and assembled, which reduces the production cost of the device itself, and so, due to the favourable price, the device becomes more widely accessible.

Figure 3:
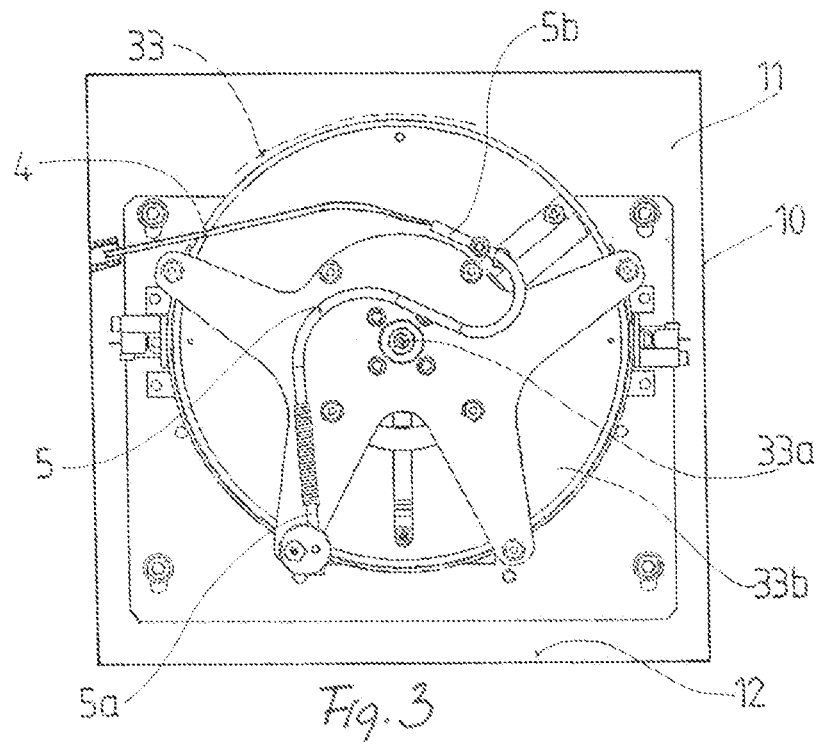
Figure 4:
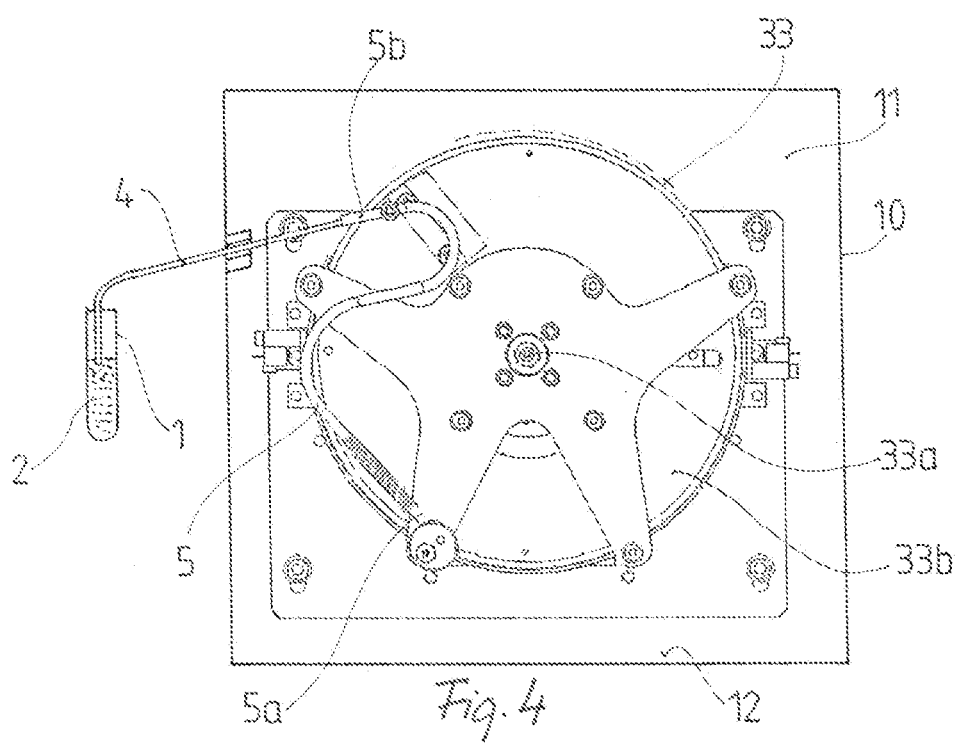

In the following we present the device according to the invention in more detail in connection with construction examples, on the basis of drawings. On the drawings FIG. 1 shows a possible version of the device according to the invention in side view, in partial cross-section, FIG. 2 shows a view of the device according to FIG. 1 from the direction II, in partial cross-section, FIG. 3 shows a view picture of the device according to the invention in partial cross-section, with the device in a given position, FIG. 4 shows a view picture of the device according to FIG. 3 in partial cross-section, with the device in a different given position, FIG. 5 shows a cross-sectional front view of the device according to the invention displaying certain phases occurring during operation.

Figure 2:
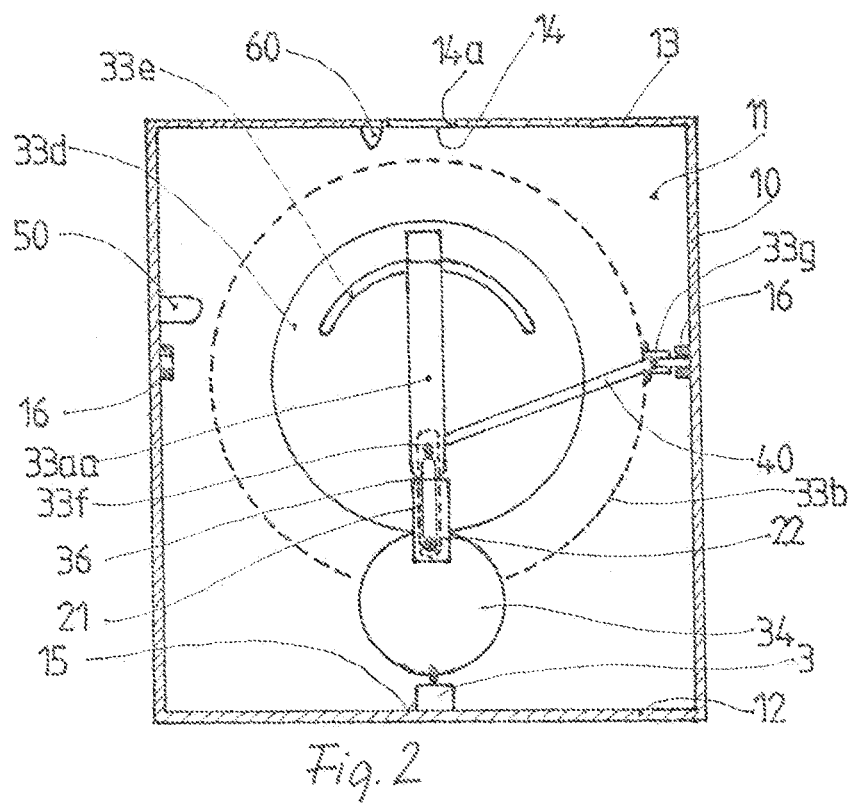

In FIGS. 1 and 2 a version of the device according to the invention may be seen that is set up as a device for taking and forwarding blood samples. It may be observed how the entire drive unit 30, the reading part-unit 50, the sensor part-unit 60, the sample-taking body 3 and the second sample-taking body 4 are contained in the internal space of the housing 10. The reading part-unit 50, the sensor part-unit 60 and the sample-taking body 3 are completely fixed to the housing 10, while the second sample-taking body 4 is inserted into the protective shell 5.

The sample-taking body 3, which is a short needle formed similarly to a standard injection needle, is fixed in the internal space 11 of the housing 10, in the lower part 12 of the housing 10, in the sample-taking zone 15, while the sensor part-unit 60 is located in the upper part 13 of the housing 10 in the filling zone 14, near to the filler passage 14a. The sample-taking body 3 makes it possible to take a determined amount from the sample 2 in the storage unit 1 located in the drive unit 30. While the task of the sensor part-unit 60 is to monitor whether a storage unit 1 containing a sample 2 is located in the device, and, in a given case, whether the storage unit 1 is opened or closed, i.e. whether there is a sealing cap on it. The task of the reading part-unit 50 is during the operation of the device to sense the label 1b on the storage unit 1, which turns in the drive unit 30, and read the identifier indicated on it. Precisely because of this the reading part-unit 50 may be in any desired place in the internal space 11 of the housing 10, one thing is important that it should be fixed in the housing 10 along the movement path of the storage unit 1 in such a way that the reading part-unit 50 is able to read the label 1b on the storage unit 1 while the storage unit 1 is moving.

As opposed to the sample-taking body 3, the reading part-unit 50 and the sensor part-unit 60, only one section 5a of the protective shell 5 if fixed to the housing 10, while the other section 5b of the protective shell 5 here is connected to the first moving element 33b of the carrying structure 33 of the drive unit 30.

Also visible on FIGS. 1 and 2 is that the drive unit 30 consists of a drive member 31 and a movement-transfer, part-unit 32, where the drive member 31 here is a single drive motor 31a, which in this case is a stepper motor, while the movement-transfer part-unit 32 consists of a carrying structure 33 and a drive transfer unit 34. The carrying structure 33 contains the first moving element 33b and the second moving element 33d. The first moving element 33b is connected to the housing 10 of the device in such a way so that it is able to rotate around rotation axle 33a, and the second moving element 33d is so connected so that it may rotate around rotation axle 33aa. Here we must note that it is not necessary for rotation axle 33a and rotation axle 33aa to be coaxial.

Here the drive transfer unit 34 of the movement-transfer part-unit 32 is a cogwheel, which is fixed onto the axle of the drive motor 31a of the drive member 31, and—in the case of this construction example—is connected to the second moving element 33d belonging to the carrying structure 33, which, in this case, is another cogwheel. In the case of the present embodiment the second control body 33e falling outside of the rotation axle 33aa is worked into the second moving element 33d, and here the second moving element 33d is also supplied with a swivel pin 33f. One of the tasks of the swivel pin 33f is to receive the sliding fitting 31 of the retaining part-unit 20, which is connected to the swivel pin 33f in such a way so that it may rotate. The retaining part-unit 20 holds the storage unit 1 inserted into the device, and ensures that it gets into the desired positions during the time spent in the internal space 11 of the housing 10, and stay there. In order to move the storage unit 1, the retaining part-unit 20 is supplied with a second guide piece 22, which works together with the first guide piece 36 of the first moving element 33b of the carrying structure 33.

In this case, the first moving element 33b is formed by a circular disc shaped plate, which is supplied with a covering 35 along its circumference. The covering 35 has an opening 35a. The first guide piece 36 is a straight-lined track in the radial direction worked into the first moving element 33b, while the second guide piece 22 is a pin able to slide in this track. Apart from the first guide piece 36 the first moving element 33b also has a first control body 33c, which first control body 33c is associated with the second control body 33e of the second moving element 33d. The second control body 33e—as is well illustrated in FIG. 2—is a slot worked in a curved way into the second moving element 33d. A piece of the pin-shaped first control body 33c of the first moving element 33b is located in the curved slot in such a way that the curved slot is unable to connect with the first control body 33c along the curve, and so the second moving element 33d rotating around rotation axle 33aa is unable to take with itself the first moving element 33b until the first end or the second end of the second control body 33e reaches the first control body 33c of the first moving element 33b.

Here we have to note that the second control body 33e and the first control body 33c may also be positioned the other way around, in other words the second control body 33e may be on the first moving element 33b, while the first control body 33c may be connected to the second moving element 33d as well. What is more, the structure of the first control body 33c and the second control body 33e may differ. The essence is that the first moving element 33b and the second moving element 33d should be in a periodical positive coupling with each other that makes it possible for the first moving element 33b or the second moving element 33d to move freely of the other for a while, and only after travelling on this path do the two structural elements rotate together.

Returning now to the swivel pin 33f, its other task is to ensure a connection for the locking structure 40. The locking structure 40 is also in connection with the diverting member 33g, which, however, here is located on the covering 35 fixed to the first moving element 33b of the carrying structure 33. This locking structure 40 is responsible for the first moving element 33b and the second moving element 33d not being able to rotate around its own rotation axle 33a and rotation axle 33aa when the carrying structure 33 is in given positions. The locking structure 40 achieves this by in given positions the locking structure 40 protrudes periodically from the diverting member 33g connected to the first moving element 33b towards the housing 10 into the fixing seats 16 formed in the housing 10, and in this way locks together the housing 10 with the carrying structure 33 so as to prevent movement.

Moving now to FIG. 3, on it a side view of the device according to the invention may be seen, which figure depicts the device after a part of the housing 10 has been removed, from the point of view of the first moving element 33b. It is well illustrated here how the second sample-taking body 4 protrudes from the protective shell 5, as well as how the second sample-taking, body 4 is positioned in the internal space 11 of the housing 10 when the device is in this position. FIG. 3 also illustrates well that the first section 5a of the protective shell 5 near to the lower part 12 of the housing is firmly fixed to the housing 10, while the second section 5b closer to the upper part 13 of the housing is fixed to the first moving element 33b of the carrying structure 33. As a consequence of this when the first moving element 33b rotates around the rotation axle 33a, the first section 5a remains stationary, while the second section 5b may rotate around the rotation axle 33a.

FIG. 4 presents that status of the device when the first moving element 33b has rotated anticlockwise around the rotation axle 33a by a given central point angle. At this time the second section 5b of the protective shell 5 gets closer to the left side of the housing 10—in the position according to FIG. 4—and then the piece of the second sample-taking body 4 located in the protective shell 5 that until then had been in the internal space 11 of the housing 10 protrudes out of the housing 10, so making it possible to take out the required amount from the sample 2 located in an open storage unit 1.

In the following the operation of the device according to the invention is presented with the help of FIG. 5. For the purpose of better understanding and comprehensibility in their entirety only the drive transfer unit 34 located in the housing 10, the second moving element 33*d*, and the retaining part-unit 20 linked to it via the swivel pin 33*f* and the sliding fitting 21, as well as the locking structure 40, and the first control body 33*c* of the first moving element 33*b* protruding into the second control body 33*e* of the second moving element 33*d* are depicted.

FIG. 5*a* presents that status of the device when the retaining part-unit 20 is in its upper dead centre position, and so the storage unit 1 protrudes but of the filler passage 14*a* located in the filler zone 14 of the housing 10, and the locking structure 40 is pushed into the fixing seat 16 of the housing 10. The swivel pin 33*f* of the second moving element 33*d* stands closer to the upper part 13 of the housing, and the sliding fitting 21 of the retaining part-unit 20 and the locking structure 40 are positioned downwards as compared to the swivel pin 33*f*. The first control body 33*c* protruding into the second control body 33*e* is located at the right-side edge of the curved slot.

When the drive motor 31*a* of the drive member 31 of the drive unit 30 starts, and starts to rotate the drive transfer unit 34, then that rotates the second moving element 33*d* clockwise around the rotation axle 33*aa* in such a way that the curved slot of the second control body 33*e* of the second moving element 33*d* does not move the first control body 33*c*. As a consequence of this only the second moving element 33*d* of the carrying structure 33 starts to rotate. The rotating second moving element 33*d* takes with it the swivel pin 33*f*, which on rotating around the rotation axle 33*aa* gets increasingly closer to the lower centre point position. While turning the swivel pin 33*f* progresses downwards and takes with it the end of the sliding fitting 21 of the locking structure 40 and the retaining part-unit 20 that is closer to the swivel pin 33*f*. Due to the force of the swivel pin 33*f* the sliding fitting 21 permits the retaining part-unit 20 downwards, and the second guide piece 22 of which fits into the first guide piece 36 of the stationary first moving element 33*b*, slides down it and determines that the retaining part-unit 20 may only descend downwards in the vertical direction in the internal space 11 of the housing 10.

By the time the swivel pin 33*f* reaches the lower centre point position while the second moving element 33*d* rotates around the rotation axle 33*aa*, the locking structure 40 is withdrawn from the fixing seat 16 of the housing 10, the retaining part-unit 20 descends into the internal space 11 of the housing 10, and takes with itself the storage unit 1, which, in this way, disappears into the filling passage 14*a* of the filling zone 14 of the housing 10, and its entire length gets into a vertical position in the internal space 11 of the housing 10. The curved slot of the second control body 33*e* rotates together with the second moving element 33*d* clockwise around the rotation axle 33*aa* so that its left edge just reaches the surface of the first control body 33*c*, i.e. of the pin of the first moving element 33*b*. This situation is presented by FIG. 5*b*.

When the drive transfer unit 34 continues to rotate in the same direction, the edge of the second control body 33*e* of the second moving element 33*d* now hits up against the first control body 33*c* of the first moving element 33*b*, and in this way grasping the first control body 33*c* with itself it starts to rotate that also around the rotation axle 33*aa*. As the first control body 33*c* is firmly fixed in the first moving element 33*b*, the first moving element 33*b* also rotates around its own rotation axle 33*a*. However, the second guide piece 22 of the retaining part-unit 20 fits into the first guide piece 36 of the first moving element 33*b*, i.e. into the straight slot, so the retaining part-unit 20, and with it the storage unit 1 also rotate clockwise. This results in that the storage unit 1 essentially approaches "the upside-down position", i.e. the sealing cap 1*a* of the storage unit 1, on the lower part 12 of the housing 10, approaches the sample-taking body 3 located in the sample-taking zone 15. This operation detail is presented by FIG. 5*c*.

Finally, during the further rotation of the drive transfer unit 34, the second moving element 33*d* rotates around-its rotation axle 33*aa* so that the swivel pin 33*f* reaches the upper centre point position. At this time the retaining part-unit 20 gets into its upper centre point position and the storage unit 1 stands vertically, with the sealing cap 1*a* turned downwards in the sample-taking zone 15 above the sample-taking body 3. In the meantime, the locking structure 40 now slides into the fixing seat 16 positioned on the left side of the housing 10, and so in this given position it stops the first moving element 33*b* as compared to the housing 10 so that it cannot rotate. FIG. 5*d* illustrates this status of the operation of the device. It can be observed that between the positions presented in FIGS. 5*b* and 5*d*, the second moving element 33*d*, and with it the swivel pin 33*f* as well as the locking structure 40 have rotated clockwise by a centre point angle of 180°.

When the storage unit 1 reaches its upside-down position, and the locking structure 40 has fixed the first moving element 33*b* as compared to the housing 10, then the drive motor 31*a* of the drive member 31 swaps direction of rotation, and so as a consequence of the rotation of the drive transfer unit 34, the second moving element 33*d* now starts to rotate anticlockwise around rotation axle 33*aa*.

Figure 5E:
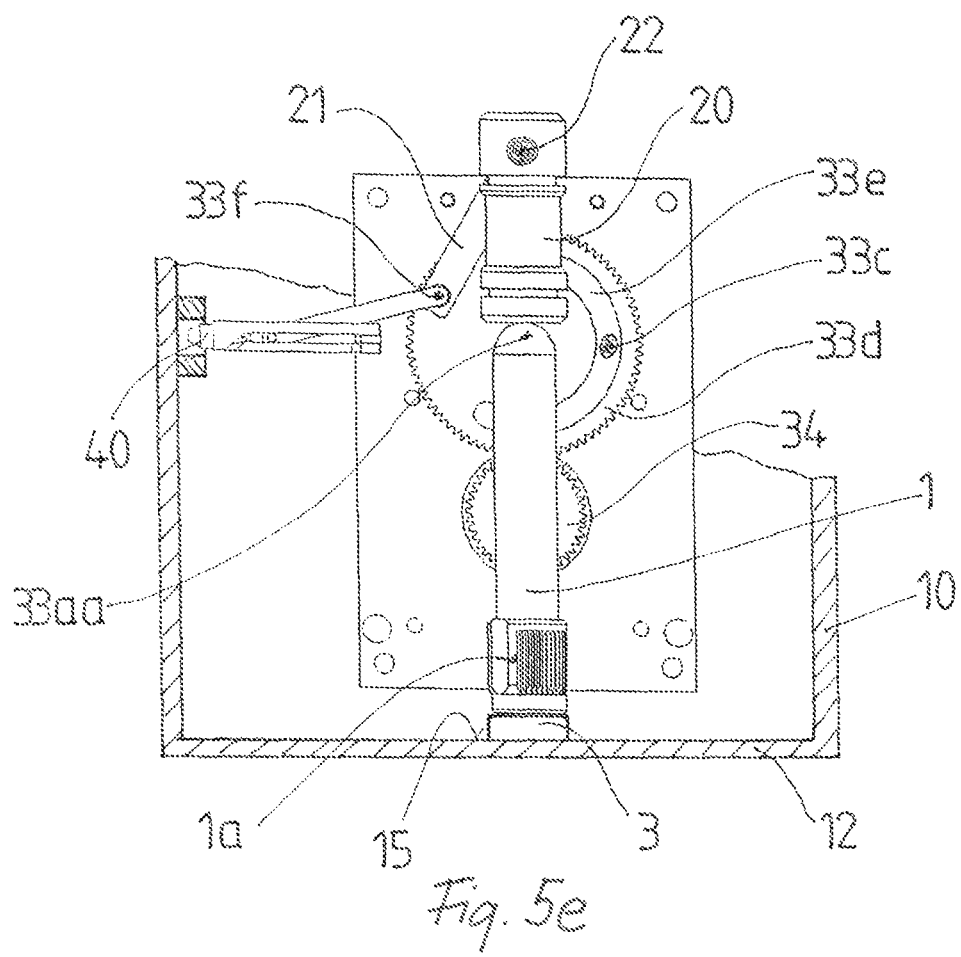

At this time the first moving element 33*b* is unable to rotate around the rotation axle 33*a*, only the second moving element 33*d* is able to rotate. As a consequence of this, however, the second control body 33*e* and the swivel pin 33*f* located in the second moving element 33*d* also turn, now in the direction opposite to its movement till then. So the swivel pin 33*f* again starts moving downwards towards the lower part 12 of the housing 10, and so takes with it the end of the locking structure 40 and the sliding fitting 21 connected to it. Due to the movement of the sliding fitting 21, it is forced to pull the retaining part-unit 20 with it, now downwards in the direction of the lower part 12 of the housing 10, and as the second guide piece 22 of the retaining part-unit 20 continues to be in a positive coupling connection with the first guide piece 36 of the first moving element 33*b*, the second guide piece 22 can only travel downwards in the first guide piece 36 formed as a vertical straight slot. Due to the movement path determined by the second guide piece 22, the retaining part-unit 20 essentially moves downwards and forces the sealing cap 1*a* of the storage unit 1 into the sample-taking body 3 fixed in the sample-taking zone 15 of the lower part 12 of the housing 10, which then takes out the required amount from the sample 2 located in the storage unit 1. The sample-taking state is shown by FIG. 5*e*. It can be seen that in this phase of the operation of the device, the first control body 33*c* continues to stand motionless, while the second control body 33*e* of the second moving element 33*d* continues to rotate anticlockwise.

After the sample taking the drive transfer unit 34 again changes direction of rotation, and as a consequence of this the second moving element 33*d* once again starts to rotate clockwise. While the second moving element 33d continues to turn due to the movement of the swivel pin 33f it achieves the position after which the sliding fitting 21 again forces the retaining part-unit upwards, and with this lifts back the storage unit 1 from the sample-taking body 3. Following this, while the second moving element 33d continues to rotate, the locking structure 40 releases from the left side fixing seat 16 of the housing 10 and terminates the inability to move of the first moving element 33b, while the left side of the second control body 33e of the second moving element 33d reaches the first control body 33c of the first moving element 33b once again. After coming into contact, the second control body 33e takes with itself the first control body 33c, and continues to rotate it in the clockwise direction; it also forces the first moving element 33b to rotate around the rotation axle 33a, also in the clockwise direction. So due to the rotation of the first moving element 33b, the storage unit 1 turns back to its basic position in such a way that the sealing cap 1a again faces upwards, and so the device reaches the state illustrated in FIG. 5a, with the difference that the first control body 33c of the first moving element 33b is now not located at the other edge of the second control body 33e of the second moving element 33d, and the storage unit 1 is in its lower "pulled in" state.

With the storage unit 1 in this position the drive transfer unit 34 again changes direction of rotation and accordingly the second moving element 33d starts to rotate around the rotation axle 33aa in the anticlockwise direction. When the second moving element 33d continues to rotate in the anticlockwise direction, the first moving element 33b does not turn, because the positive coupling connection between the first control body 33c and the second control body 33e is temporarily terminated. However, on the effect of the rotation of the second moving element 33d, the locking structure 40 again protrudes into the right side fixing seat 16 of the housing 10, it again excludes even the possibility of the first moving element 33b moving, and as a consequence of the positive coupling connection between the second guide piece 22 and the first guide piece 36 of the first moving element 33b the retaining part-unit 20 lifts out the storage unit 1 through the opening 35a of the covering 35, and though the filling passage 14a of the upper part 13 of the housing 10, from the internal space 11 of the housing 10.

Here we must note that the drive transfer unit 34 may also be adjusted so that following sample-taking it does not issue the now unnecessary storage unit 1 after returning to the position shown in FIG. 5a, but in an interim state. This, however, is not of interest from the point of view of the sphere of protection of the invention.

It is also obvious that the changing of the direction of rotation of the drive transfer unit 34 is controlled by a control unit—not detailed here—however the control itself is not closely related to the essence of the invention, so we do not deal with it in detail here. However, it should be mentioned that with the help of the control it may also be solved that by using the drive unit 30 according to the invention before sample-taking the storage unit 1 may be moved so as to mix and so homogenise the sample 2.

It must also be mentioned that when switching on the device the sensor part-unit 60 is also activated, and monitors whether there is a storage unit 1 in the filler passage 14a of the filler zone 14 of the housing 10 or not, and if there is, whether it has a sealing cap 1a on it. If it does not sense a sealing cap 1a on the storage unit 1 in the filler passage 14a, then it does not permit the drive member 31 of the drive unit 30 to switch on and rotate the drive transfer unit 34.

If there is no storage unit 1 in the filler passage 14a and the device is instructed to perform sampling, then the drive motor 31a of the drive member 31 of the drive unit 30 in the position according to FIG. 5a, but naturally without the storage unit 1, does not start to rotate so it rotates the second moving element 33d in the clockwise direction around the rotation axle 33aa, but in the opposite direction, in the anticlockwise direction. In this way the carrying structure 33 goes from the position visible in FIG. 3 to the position visible in FIG. 4. While the carrying structure 33 is rotating, the first moving element 33b rotates around the rotation axle 33a in such a way that it takes with it the second section 5b of the protective shell 5, while the first section 5a of the protective shell 5 is fixed to the housing 10—as can be seen in FIG. 4—it only rotates, i.e. it does not change its position only its status.

On the effect of this rotation, the second section 5b of the protective shell 5 gets closer to the left hand edge of the housing 10, and so the second sample-taking body 4 in the protective shell 5 protrudes out of the internal space 11 of the housing 10 to outside the housing 10 making it possible for the second sample-taking body 4 to reach the storage unit 1 outside the housing 10, which storage unit 1 is not covered with a sealing cap 1a, and so the second sample-taking body 4 made as a tube from a flexible material, e.g. Teflon, can easily get into the storage unit 1 and reach the sample 2 in it. After sample-taking the drive motor 31a of the drive member 31 of the drive unit 30 changes direction of rotation, it rotates the drive-transfer unit 34 in the other direction, which starts to rotate the second moving element 33d and with it the entire carrying structure 33 in the clockwise direction around the rotation axle 33a until it gets into the position visible in FIG. 3. At this time the second sample-taking body 4 in the protective shell 5 is withdrawn into the internal space 11 of the housing 10. During rotation in any direction of the carrying structure 33 of the device the reading part-unit 50 fixed in the internal space 11 of the housing 10 is also activated and if a storage unit 1 passes in front of it, then it reads the marking on the label 1b located on the storage unit 1, which—in the case of a suitably set up programme—is associated to the result of the sample 2 taken from the given storage unit 1.

The device according to the invention may be used to good effect in all cases when a storage unit 1 containing a liquid sample 2 has to be handled and the sample has to be taken out of it either in part or in its entirety quickly, simply, safely and with a small amount of energy.

List of references

| | |
|---|---|
| 1 storage unit | 1a sealing cap |
| | 1b label |
| 2 sample | |
| 3 sample-taking body | |
| 4 second sample-taking body | |
| 5 protective shell | 5a first section |
| | 5b second section |
| 10 housing | 11 internal space |
| | 12 lower part |
| | 13 upper part |
| | 14 filling zone |
| | 14a filler passage |
| | 15 sample-taking zone |
| | 16 fixing seat |
| 20 retaining part-unit | 21 sliding fitting |
| | 22 second guide piece |
| 30 moving unit | 31 drive member |
| | 31a drive motor |
| | 32 movement-transfer part-unit |

-continued

List of references 33 carrying structure
33a rotation axle
33aa rotation axle
33b first moving element
33c first control body
33d second moving element
33e second control body
33f swivel pin
33g diverting member
34 drive-transfer unit
35 covering
35a opening
36 first guide piece
40 locking structure
50 reading part-unit
60 sensor part-unit

The invention claimed is:

1. A device for handling a sample containing liquid components so as to perform sample-taking from blood, said device comprising:
 a housing encompassing the device;
 a retaining part-unit for holding a storage unit containing the sample;
 a drive unit for moving the retaining part-unit; and
 at least one sample-taking body located in an internal space of the housing;
 wherein the drive unit has a drive member and a movement-transfer part-unit connected to the drive member, and wherein the movement-transfer part-unit has at least one rotation axle; and
 wherein the drive member of the drive unit has a single drive motor, while the movement-transfer part-unit includes a carrying structure which rotates around said at least one rotation axle of the movement-transfer part-unit;
 said device further comprising a drive-transfer unit inserted between the carrying structure and the drive motor, the carrying structure having a first moving element and a second moving element;
 wherein the first moving element has a first control body falling outside of a first rotation axle, while the second moving element has a second control body working together with the first control body and falling outside of a second rotation axle;
 wherein, with the help of the second control body working together with the first control body, the first moving element and the second moving element have a periodical, movement-transfer positive coupling link with each other;
 wherein one of the first moving element and the second moving element of the carrying structure is connected to a sliding fitting connected to the retaining part-unit serving to hold the storage unit, one of the first moving element and the second moving element of the carrying structure having a first guide piece, the retaining part-unit serving to hold the storage unit, the sliding fitting having a second guide piece, the first guide piece and the second guide piece being connected to one another, and the storage unit being periodically forced to a movement path in this way, while one of the first moving element and the second moving element is supplemented with a swivel pin falling outside of a rotation axle of the swivel pin;
 wherein at least one of the sliding fitting connected to the retaining part-unit and a locking structure is connected to the swivel pin in such a way as to permit rotation;
 wherein the locking structure is inserted between one of the first moving element and the second moving element of the carrying structure disposed on one side of the locking structure and the housing disposed on another side of the locking structure; and
 wherein, with the help of the locking structure, one of the first moving element and the second moving element is temporarily connected to the housing, the sample-taking body is in the internal space of the housing located with respect to the housing, and the sample-taking body is fixed in a lower part of the housing.

2. The device according to claim 1, wherein the sample-taking body is a needle.

3. The device according to claim 2, further comprising a second sample-taking body, wherein at least a part of the second sample-taking body is inserted into a protective shell located in the housing, and one section of the protective shell is fixed to the housing, while a second section of the protective shell is fixed to the carrying structure that is capable of moving as compared to the housing.

4. The device according to claim 3, wherein the second sample-taking body is a flexible tube.

5. The device according to claim 4, further comprising a reading part-unit located in the internal space of the housing in the vicinity of a movement path of the storage unit containing the sample.

6. The device according to claim 4, further comprising a sensor part-unit located in an internal space of the housing in the vicinity of a filling zone of the storage unit containing the sample.

7. The device according to claim 3, further comprising a sensor part-unit located in the internal space of the housing in the vicinity of a filling zone of the storage unit containing the sample.

8. The device according to claim 2, further comprising a reading part-unit located in the internal space of the housing in the vicinity of a movement path of the storage unit containing the sample.

9. The device according to claim 8, further comprising a sensor part-unit located in the internal space of the housing in the vicinity of a filling zone of the storage unit containing the sample.

10. The device according to claim 2, further comprising a sensor part-unit located in the internal space of the housing in the vicinity of a filling zone of the storage unit containing the sample.

11. The device according to claim 1, further comprising a second sample-taking body, wherein at least a part of the second sample-taking body is inserted into a protective shell located in the housing, and one section of the protective shell is fixed to the housing, while a second section of the protective shell is fixed to the carrying structure that is capable of moving as compared to the housing.

12. The device according to claim 11, wherein the second sample-taking body is a flexible tube.

13. The device according to claim 12, further comprising a reading part-unit located in the internal space of the housing in the vicinity of a movement path of the storage unit containing the sample.

14. The device according to claim 12, further comprising a sensor part-unit located in the internal space of the housing in the vicinity of a filling zone of the storage unit containing the sample.

15. The device according to claim 11, further comprising a reading part-unit located in the internal space of the housing in the vicinity of a movement path of the storage unit containing the sample.

16. The device according to claim 15, further comprising a sensor part-unit located in the internal space of the housing in the vicinity of a filling zone of the storage unit containing the sample.

17. The device according to claim 11, further comprising a sensor part-unit located in the internal space of the housing in the vicinity of a filling zone of the storage unit containing the sample.

18. The device according to claim 1, further comprising a reading part-unit located in the internal space of the housing in the vicinity of a movement path of the storage unit containing the sample.

19. The device according to claim 18, further comprising a sensor part-unit located in the internal space of the housing in the vicinity of a filling zone of the storage unit containing the sample.

20. The device according to claim 1, further comprising a sensor part-unit located in the internal space of the housing in the vicinity of a filling zone of the storage unit containing the sample.

* * * * *